United States Patent
Peppel

(10) Patent No.: US 7,615,035 B2
(45) Date of Patent: Nov. 10, 2009

(54) NEEDLELESS ACCESS PORT VALVES

(75) Inventor: Peter W. Peppel, Nazareth, PA (US)

(73) Assignee: B. Braun Medical Inc., Bethlehem, PA (US)

( * ) Notice: Subject to any disclaimer, the term of this patent is extended or adjusted under 35 U.S.C. 154(b) by 562 days.

(21) Appl. No.: 11/088,303

(22) Filed: Mar. 24, 2005

(65) Prior Publication Data

US 2006/0229571 A1    Oct. 12, 2006

(51) Int. Cl.
A61M 37/00    (2006.01)
A61M 5/14     (2006.01)
A61M 5/00     (2006.01)

(52) U.S. Cl. ........................................ 604/256; 604/86

(58) Field of Classification Search ................ 604/256, 604/86, 248, 263, 264, 523, 88, 170.03, 167.02, 604/167.05, 201, 242, 243, 288.02, 205, 604/206

See application file for complete search history.

(56) References Cited

U.S. PATENT DOCUMENTS

| | | | |
|---|---|---|---|
| 1,831,668 A * | 11/1931 | Juhl ............................ 604/183 |
| 4,197,848 A | 4/1980 | Garrett et al. |
| 4,535,819 A | 8/1985 | Atkinson et al. |
| 4,765,588 A | 8/1988 | Atkinson |
| 4,934,655 A | 6/1990 | Blenkush et al. |
| 4,953,594 A | 9/1990 | Von Berg |
| 5,006,114 A | 4/1991 | Rogers et al. |
| 5,049,128 A | 9/1991 | Duquette |
| 5,065,783 A | 11/1991 | Ogle, II |
| 5,104,389 A | 4/1992 | Deem et al. |
| 5,108,380 A | 4/1992 | Herlitze et al. |
| 5,147,333 A | 9/1992 | Raines |
| 5,158,554 A * | 10/1992 | Jepson et al. ................ 604/539 |
| 5,163,922 A | 11/1992 | McElveen, Jr. et al. |
| 5,171,234 A * | 12/1992 | Jepson et al. ................ 604/534 |
| 5,188,620 A * | 2/1993 | Jepson et al. ................ 604/534 |
| 5,199,948 A * | 4/1993 | McPhee ........................ 604/86 |
| 5,203,775 A | 4/1993 | Frank et al. |
| 5,226,879 A * | 7/1993 | Ensminger et al. ...... 604/288.03 |
| 5,230,706 A | 7/1993 | Duquette |
| 5,242,393 A | 9/1993 | Brimhall et al. |
| 5,242,423 A | 9/1993 | Goodsir et al. |
| 5,251,873 A | 10/1993 | Atkinson et al. |
| 5,269,771 A | 12/1993 | Thomas et al. |
| 5,281,206 A | 1/1994 | Lopez |
| 5,289,849 A | 3/1994 | Paradis |
| 5,330,450 A | 7/1994 | Lopez |
| 5,334,188 A * | 8/1994 | Inoue et al. .................. 604/539 |
| 5,344,414 A | 9/1994 | Lopez et al. |
| 5,353,837 A | 10/1994 | Faust |
| 5,360,413 A | 11/1994 | Leason et al. |
| 5,380,306 A | 1/1995 | Brinon |
| 5,389,086 A * | 2/1995 | Attermeier et al. .......... 604/242 |
| 5,390,898 A | 2/1995 | Smedley et al. |
| 5,395,348 A | 3/1995 | Ryan |
| 5,401,245 A | 3/1995 | Haining |
| 5,423,791 A | 6/1995 | Bartlett |
| 5,425,465 A | 6/1995 | Healy |
| 5,439,451 A | 8/1995 | Collinson et al. |
| 5,441,487 A | 8/1995 | Vedder |

(Continued)

*Primary Examiner*—Kevin C Sirmons
*Assistant Examiner*—Michael J Anderson
(74) *Attorney, Agent, or Firm*—Klein, O'Neill & Singh, LLP

(57) ABSTRACT

Needleless access port valves are generally discussed herein with particular discussions extended to needleless access port valves comprising an inlet coupler. In accordance with aspects of the present invention, a coupler comprises an inlet and an outlet. The inlet is adapted to mate with a first medical implement and the outlet is adapted to mate with an inlet of a valve, which has an outlet adapted to mate with a second medical implement.

30 Claims, 2 Drawing Sheets

U.S. PATENT DOCUMENTS

| | | | |
|---|---|---|---|
| 5,462,255 A | 10/1995 | Rosen et al. | |
| 5,466,219 A | 11/1995 | Lynn et al. | |
| 5,480,393 A * | 1/1996 | Bommarito | 604/523 |
| 5,501,676 A * | 3/1996 | Niedospial et al. | 604/534 |
| 5,509,433 A | 4/1996 | Paradis | |
| 5,509,912 A | 4/1996 | Vaillancourt et al. | |
| 5,520,661 A * | 5/1996 | Lal et al. | 604/246 |
| 5,533,708 A * | 7/1996 | Atkinson et al. | 251/149.1 |
| 5,533,983 A | 7/1996 | Haining | |
| 5,535,771 A | 7/1996 | Purdy et al. | |
| 5,535,785 A | 7/1996 | Werge et al. | |
| 5,540,661 A | 7/1996 | Tomisaka et al. | |
| 5,549,577 A | 8/1996 | Siegel et al. | |
| 5,569,235 A | 10/1996 | Ross et al. | |
| 5,573,516 A | 11/1996 | Tyner | |
| 5,584,808 A | 12/1996 | Healy | |
| 5,616,129 A | 4/1997 | Mayer | |
| 5,616,130 A * | 4/1997 | Mayer | 604/167.02 |
| 5,620,434 A | 4/1997 | Brony | |
| 5,624,414 A | 4/1997 | Boettger | |
| 5,645,538 A | 7/1997 | Richmond | |
| 5,657,963 A * | 8/1997 | Hinchliffe et al. | 251/149.1 |
| 5,674,206 A | 10/1997 | Allton et al. | |
| 5,676,346 A | 10/1997 | Leinsing | |
| 5,685,866 A | 11/1997 | Lopez | |
| 5,690,612 A | 11/1997 | Lopez et al. | |
| 5,694,686 A | 12/1997 | Lopez | |
| 5,695,466 A | 12/1997 | Lopez et al. | |
| 5,699,821 A | 12/1997 | Paradis | |
| 5,700,248 A | 12/1997 | Lopez | |
| 5,716,347 A * | 2/1998 | Gibbs et al. | 604/247 |
| 5,730,418 A | 3/1998 | Feith et al. | |
| 5,738,663 A | 4/1998 | Lopez | |
| 5,743,894 A | 4/1998 | Swisher | |
| 5,776,113 A | 7/1998 | Daugherty et al. | |
| 5,782,816 A | 7/1998 | Werschmidt et al. | |
| 5,785,693 A | 7/1998 | Haining | |
| 5,788,215 A * | 8/1998 | Ryan | 251/149.6 |
| 5,806,551 A | 9/1998 | Meloul et al. | |
| 5,806,831 A | 9/1998 | Paradis | |
| 5,810,768 A | 9/1998 | Lopez | |
| 5,810,792 A | 9/1998 | Fangrow, Jr. et al. | |
| 5,810,793 A | 9/1998 | Boettger | |
| 5,814,024 A * | 9/1998 | Thompson et al. | 604/246 |
| 5,833,674 A * | 11/1998 | Turnbull et al. | 604/533 |
| 5,839,715 A | 11/1998 | Leinsing | |
| 5,843,046 A * | 12/1998 | Motisi et al. | 604/256 |
| 5,848,994 A | 12/1998 | Richmond | |
| 5,860,962 A * | 1/1999 | Lewandowski et al. | 604/263 |
| 5,873,862 A | 2/1999 | Lopez | |
| 5,901,942 A | 5/1999 | Lopez | |
| 5,921,264 A | 7/1999 | Paradis | |
| 5,921,419 A | 7/1999 | Niedospial, Jr. et al. | |
| 5,928,204 A | 7/1999 | Lopez | |
| 5,954,104 A * | 9/1999 | Daubert et al. | 141/329 |
| 5,957,898 A | 9/1999 | Jepson et al. | |
| 5,967,490 A | 10/1999 | Pike | |
| 5,971,950 A | 10/1999 | Lopez et al. | |
| 5,971,965 A * | 10/1999 | Mayer | 604/249 |
| 6,019,748 A | 2/2000 | Lopez | |
| 6,029,946 A | 2/2000 | Doyle | |
| 6,036,171 A | 3/2000 | Weinheimer et al. | |
| 6,039,302 A | 3/2000 | Cote, Sr. et al. | |
| 6,045,534 A | 4/2000 | Jacobsen et al. | |
| 6,050,978 A * | 4/2000 | Orr et al. | 604/249 |
| 6,063,062 A | 5/2000 | Paradis | |
| 6,068,011 A | 5/2000 | Paradis | |
| 6,083,194 A | 7/2000 | Lopez | |
| 6,106,502 A | 8/2000 | Richmond | |
| 6,113,068 A | 9/2000 | Ryan | |
| 6,117,114 A | 9/2000 | Paradis | |
| 6,127,320 A | 10/2000 | van Ooij et al. | |
| 6,132,403 A | 10/2000 | Lopez | |
| 6,132,404 A | 10/2000 | Lopez | |
| 6,142,446 A | 11/2000 | Leinsing | |
| 6,146,362 A * | 11/2000 | Turnbull et al. | 604/256 |
| 6,168,137 B1 | 1/2001 | Paradis | |
| 6,170,800 B1 | 1/2001 | Meloul et al. | |
| 6,171,287 B1 | 1/2001 | Lynn et al. | |
| 6,189,859 B1 | 2/2001 | Rohrbough et al. | |
| 6,228,069 B1 | 5/2001 | Barth et al. | |
| 6,245,048 B1 | 6/2001 | Fangrow, Jr. et al. | |
| 6,245,056 B1 | 6/2001 | Walker et al. | |
| 6,261,282 B1 | 7/2001 | Jepson et al. | |
| 6,273,869 B1 | 8/2001 | Vaillancourt | |
| 6,290,206 B1 | 9/2001 | Doyle | |
| 6,290,688 B1 | 9/2001 | Lopez et al. | |
| 6,299,131 B1 | 10/2001 | Ryan | |
| 6,299,132 B1 | 10/2001 | Weinheimer et al. | |
| 6,325,782 B1 | 12/2001 | Lopez | |
| 6,344,033 B1 | 2/2002 | Jepson et al. | |
| 6,364,869 B1 | 4/2002 | Bonaldo | |
| 6,428,520 B1 | 8/2002 | Lopez et al. | |
| 6,482,188 B1 | 11/2002 | Rogers et al. | |
| 6,491,668 B1 | 12/2002 | Paradis | |
| 6,541,802 B2 | 4/2003 | Doyle | |
| 6,572,592 B1 | 6/2003 | Lopez | |
| 6,585,229 B2 | 7/2003 | Cote, Sr. et al. | |
| 6,599,273 B1 | 7/2003 | Lopez | |
| 6,616,627 B2 | 9/2003 | Willis et al. | |
| 6,626,418 B2 | 9/2003 | Kiehne | |
| 6,635,044 B2 | 10/2003 | Lopez | |
| 6,641,561 B1 | 11/2003 | Hill et al. | |
| 6,645,170 B2 | 11/2003 | Landau | |
| 6,669,673 B2 | 12/2003 | Lopez | |
| 6,669,681 B2 | 12/2003 | Jepson et al. | |
| 6,682,509 B2 | 1/2004 | Lopez | |
| 6,695,817 B1 | 2/2004 | Fangrow, Jr. | |
| 6,706,022 B1 | 3/2004 | Leinsing et al. | |
| 6,709,418 B1 * | 3/2004 | Aboul-Hosn et al. | 604/158 |
| 6,709,424 B1 * | 3/2004 | Knierbein | 604/411 |
| 6,755,391 B2 | 6/2004 | Newton et al. | |
| 6,758,833 B2 | 7/2004 | Lopez | |
| 6,802,490 B2 | 10/2004 | Leinsing et al. | |
| 6,808,161 B1 * | 10/2004 | Hishikawa | 251/149.1 |
| 6,840,501 B2 | 1/2005 | Doyle | |
| 6,855,138 B2 | 2/2005 | Tsai | |
| 6,869,426 B2 | 3/2005 | Ganem | |
| 6,871,838 B2 | 3/2005 | Raines et al. | |
| 6,932,795 B2 * | 8/2005 | Lopez et al. | 604/249 |
| 7,040,598 B2 * | 5/2006 | Raybuck | 251/149.1 |
| 7,100,890 B2 * | 9/2006 | Cote et al. | 251/149.1 |
| 2001/0016715 A1 * | 8/2001 | Mayer | 604/249 |
| 2001/0045539 A1 * | 11/2001 | Doyle | 251/149.1 |
| 2002/0082586 A1 * | 6/2002 | Finley et al. | 604/535 |
| 2002/0133124 A1 * | 9/2002 | Leinsing et al. | 604/256 |
| 2002/0193752 A1 * | 12/2002 | Lynn | 604/249 |
| 2003/0060779 A1 * | 3/2003 | Richmond | 604/256 |
| 2003/0105452 A1 * | 6/2003 | Mayer | 604/256 |
| 2003/0199835 A1 * | 10/2003 | Leinsing et al. | 604/256 |
| 2004/0006330 A1 * | 1/2004 | Fangrow, Jr. | 604/533 |
| 2004/0158211 A1 * | 8/2004 | Rogers et al. | 604/284 |
| 2004/0171993 A1 * | 9/2004 | Bonaldo | 604/248 |
| 2004/0172006 A1 * | 9/2004 | Bonaldo | 604/523 |
| 2004/0199126 A1 * | 10/2004 | Harding et al. | 604/256 |
| 2005/0121638 A1 * | 6/2005 | Doyle | 251/149 |
| 2005/0228362 A1 * | 10/2005 | Vaillancourt | 604/533 |
| 2005/0261637 A1 * | 11/2005 | Miller | 604/256 |
| 2006/0155258 A1 * | 7/2006 | Rogers et al. | 604/508 |
| 2006/0271016 A1 * | 11/2006 | Fangrow | 604/539 |
| 2007/0179609 A1 * | 8/2007 | Goble et al. | 623/16.11 |
| 2007/0225648 A1 * | 9/2007 | Winsor et al. | 604/167.04 |

* cited by examiner

NEEDLELESS ACCESS PORT VALVES

Needleless access port valves are generally discussed herein with particular discussions extended to needleless access port valves comprising an inlet coupler.

BACKGROUND

Needleless access port valves are widely used in the medical industry for accessing an IV line and/or the internals of a patient or subject. Generally speaking, prior art valves utilize a valve housing in combination with a moveable internal plug or piston to control the flow of fluid through a valve. The plug or piston may be moved by a syringe or a medical implement to open the inlet of the valve for accessing the interior cavity of the valve. When a fluid is delivered through the valve, fluid flow typically flows around the outside of the plug or piston in the direction towards the outlet. Upon removal of the syringe or medical implement, the plug or piston returns to its original position, either un-aided or aided by a biasing means, such as a spring or a diaphragm.

In some prior art valves, when the syringe or medical implement pushes the plug or piston, the plug or piston is pierced by a piercing device, such as a spike. The spike typically incorporates one or more fluid channels for fluid flow flowing through the pierced piston and then through the fluid channels in the spike. In yet other prior art valves, a self-flushing or positive flush feature is incorporated to push residual fluids confined inside the interior cavity of the valve to flow out the outlet when the syringe or medical implement is removed.

While prior art needleless access port valves are viable options for their intended applications, there remains a need for alternative needleless access port valves.

SUMMARY

The present invention may be implemented by providing a needleless access port valve assembly comprising a coupler comprising an inlet and an outlet and a valve comprising an inlet and an outlet; wherein the outlet of the coupler comprises a port comprising a curved section and the inlet of the valve comprises a septum and wherein the septum is configured to receive the port and the curved section of the port is configured to rotate relative to the septum.

In another aspect of the present invention, there is provided a needleless access port valve assembly comprising a coupler matingly engaged to a valve; the coupler comprising an inlet for mating with a first medical implement and the valve comprising an outlet for mating with a second medical implement, wherein the engagement between the coupler and the valve comprises a port comprising a flow section having a fluid opening projecting through a septum and rotating the flow section relative to the septum.

In yet another aspect of the present invention, there is provided a needleless access port valve assembly comprising a coupler matingly engaged to a valve, the coupler comprising an output means for outputting fluid flow and for engaging the valve; the valve comprising a connection means for receiving the output means, wherein the output means is rotatable relative to the connection means; and wherein the coupler further comprising an inlet for engaging a first medical implement and the valve comprising an outlet for engaging a second medical implement.

Other aspects and variations of the valve assemblies summarized above are also contemplated and will be more fully understood when considered with respect to the following disclosure.

BRIEF DESCRIPTION OF THE DRAWINGS

These and other features and advantages of the present invention will become appreciated as the same become better understood with reference to the specification, claims and appended drawings wherein:

DETAILED DESCRIPTION

The detailed description set forth below in connection with the appended drawings is intended as a description of the presently preferred embodiments of needleless access port valves or backcheck valves (herein "valves") provided in accordance with aspects of the present invention and is not intended to represent the only forms in which the present invention may be constructed or utilized. The description sets forth the features and the steps for constructing and using the valves of the present invention in connection with the illustrated embodiments. It is to be understood, however, that the same or equivalent functions and structures may be accomplished by different embodiments that are also intended to be encompassed within the spirit and scope of the invention. As denoted elsewhere herein, like element numbers are intended to indicate like or similar elements or features.

Figure 1:
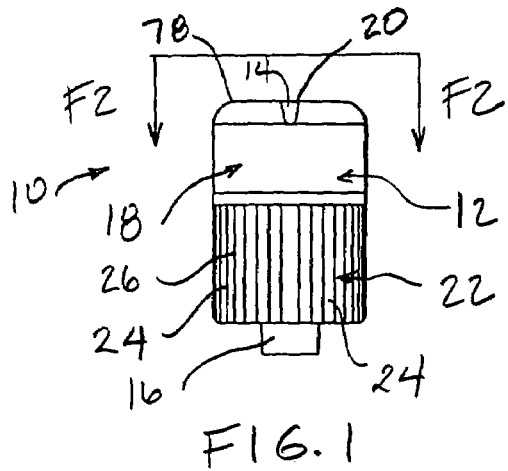
FIG. 1 is a semi-schematic side view of a needleless access port valve provided in accordance with aspects of the present invention.
Figure 2:
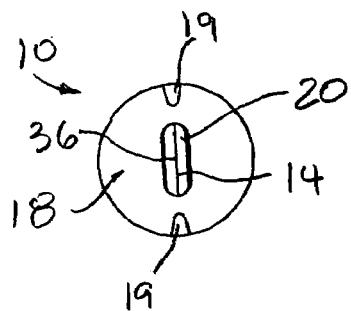
FIG. 2 is a semi-schematic top view of the valve of FIG. 1 taken along line F2-F2.

Referring now to FIG. 1, a semi-schematic side view of a needleless access port valve provided in accordance with aspects of the present invention is shown, which is generally designated 10. In one exemplary embodiment, the valve 10 comprises a housing 12 comprising an inlet 14 and an outlet 16. In a preferred embodiment, an upper housing part 18 is formed with an opening 20 defining the inlet 14. With reference to FIG. 2, which is a top view of the valve 10 of FIG. 1 taken along line F2-F2, the opening 20 has a non-circular configuration and in one exemplary embodiment is an elongated opening comprising a generally linear central region comprising two rounded ends. However, other shaped openings such as a triangular opening, a rectangular opening, a square opening, an oval opening, or a circular shaped opening may be incorporated without deviating from the spirit and scope of the present invention provided they are appropriately sized to receive an outlet of an inlet coupler, as further discussed below. Two notches or indentations 19 may optionally be incorporated for providing an indicia or alignment with the fins (60 of FIG. 4) for removing an inserting the inlet coupler (52 of FIG. 4) into the inlet 14.

Referring again to FIG. 1, the upper housing part 18 is attached to a lower housing part 22, which in one exemplary embodiment comprises a plurality of spaced apart projections 24 for gripping purposes. However, a smooth outer surface or other shaped projections, such as a round shape, may be incorporated without deviating from the spirit and scope of the present invention. In one exemplary embodiment, the lower housing part 22 comprises a threaded shroud 26 and the outlet 16, which form a standard threaded male luer adapted to mate with a corresponding threaded luer fitting, such as a catheter assembly or other medical implement.

In accordance with aspects of the present invention, the upper and lower housing parts are separately molded and subsequently assembled and secured to one another by welding or adhesive. In addition thereto or alternatively, the two parts may be assembled to one another using an interference fit. The housing components are preferably molded from a soft plastic material, such as ethylene vinyl acetate (EVA), high density polyethylene (HDPE), low density polyethylene (LDPE or LLDPE), or polypropylene (PP). More preferably, a rigid plastic is used to form the housing components. Most preferably, polycarbonate is used to form the housing components. However, other rigid plastics may be tested and incorporated without deviating from the spirit and scope of the present invention. A semi-opaque or an opaque finish having a colored tone may be incorporated. Preferably, however, a clear translucent finish is incorporated.

Figure 3:
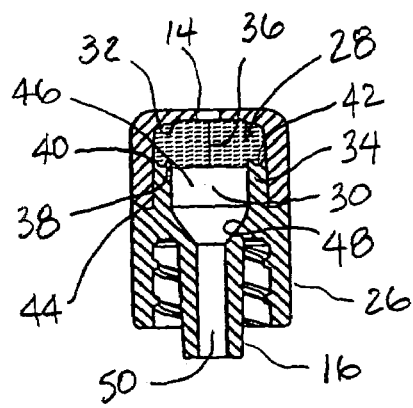
FIG. 3 is a semi-schematic cross-sectional side view of the valve of FIG. 1.

Referring now to FIG. 3, a semi-schematic cross-sectional side view of the valve 10 of FIG. 1 is shown. In one exemplary embodiment, a rubber septum 28 is disposed in an upper interior cavity section 30 of the housing 12 and is bounded therein by the interior wall surface 32 of the upper housing part 18 and a projecting collar 34 of the lower housing part 22. In a preferred embodiment, the rubber septum 28 is sized slightly larger than the cavity in which it sits so that it is compressed by the interior wall surface 32 and the collar 34 when situated therebetween. The septum 28 comprises a slit 36 and the compressive force generated by the relative dimensions of the septum and the interior cavity 30 facilitates the closing of the slit when the same is opened by an inlet coupler, as further discussed below. The septum 28 may be made from a butyl rubber or a Polytetrafluoroethylene (PTFE) material. The septum may also be made from a polyisoprene material. However, other materials may be tested and implemented without deviating from the spirit and scope of the present invention.

While a generally flat surface to surface contact between the various valve components may be incorporated, in a preferred embodiment, several tapered surfaces are incorporated to provide a preferred taper contact. For example, the end edge 38 of the collar 34 incorporates two races 40 defining a groove 42 therebetween for gripping the septum 28 in a tongue-and-groove-like configuration. Similarly, the contact seam 44 between the upper housing part 18 and the lower housing part 22 comprises a tapered contact.

Interiorly, the cavity 30 subjacent the septum 28 comprises an upper cavity section 46, a taper section 48, and a generally cylindrical lumen 50 defined by the outlet duct 16. The cavity 30 is isolated from the inlet 14 when the slit 36 is in a closed position as shown in FIG. 3.

Figure 4:
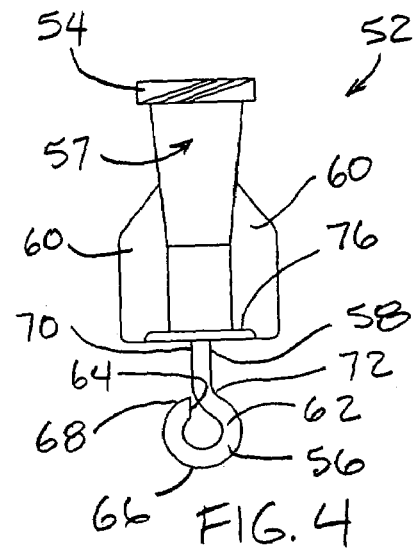
FIG. 4 is a semi-schematic side view of a valve coupler provided in accordance with aspects of the present invention.

FIG. 4 is a semi-schematic side view of a inlet coupler 52 provided in accordance with aspects of the present invention. The inlet coupler 52 functions as a conduit or a link for fluid communication between a first medical implement (not shown), such as a syringe, and a second medical implement (not shown) connected to the valve 10. In one exemplary embodiment, the coupler 52 comprises an inlet 54 and an outlet 56. More specifically, the coupler 52 comprises a housing 57 comprising a threaded female luer defining the inlet 54 and a tubing 58 defining the outlet 56. A pair of ribs 60 may be incorporated to structurally reinforce the housing 57, which also serves as gripping members for gripping the coupler 52.

In one exemplary embodiment, the tubing 58 comprises a curve section 62. In a preferred embodiment, the tubing 58 incorporates an eye-hook shape and comprises an outlet opening 64 positioned proximally of a lower curve section 66. Accordingly, fluid flow flowing through the tubing 58 travels through the curve section 62, the lower curve section 66, then proximally upwardly out the outlet opening 64. The upper edge 68 of the outlet opening 64 and the intersection between the curve section 62 and the upper tubing section 70 lie generally along an arc circle of the eye-hook shape outlet 56. As further discussed below, these sections 68, 72 of the outlet 56 serve as pivoting points when the outlet 56 is rotated to interlock the outlet 56 to the septum 28.

In one exemplary embodiment, the tubing 58 is made from a metal material and the housing 57 from a rigid plastic. In a preferred embodiment, the metal is a stainless steel material and the housing is made from polycarbonate, which is over molded to the tubing. The housing 57 may incorporate a same clear finish as the valve housing 10.

In an alternatively embodiment, the inlet coupler 52 is a one-piece molded plastic part with the outlet tubing 58 molded from the same material. In the alternative embodiment, the shape of the outlet tubing 58 may comprise a continuous loop having an opening or a hole for passing fluid. In yet another alternative embodiment, the outlet tubing can embody an upside down "T" shape configuration or a "L" shape configuration with tapered edges for contacting the septum.

Figure 5:
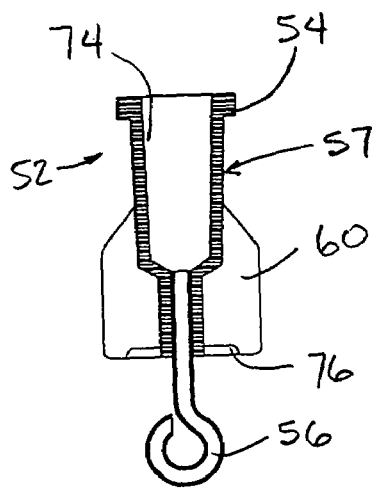
FIG. 5 is a semi-schematic cross-sectional side view of the valve coupler of FIG. 4.

FIG. 5 is a semi-schematic side view of the coupler 52 of FIG. 4. The coupler has a luer taper 74 at the inlet 54 for mating with a corresponding taper on a medical implement (not shown), such as a syringe tip. A base or a flange 76 is incorporated at the distal base of the housing 57. The flange 76 is configured to abut the top surface 78 of the first housing part 18 when the two couple together to provide fluid pathway through the valve 10.

Figure 6:
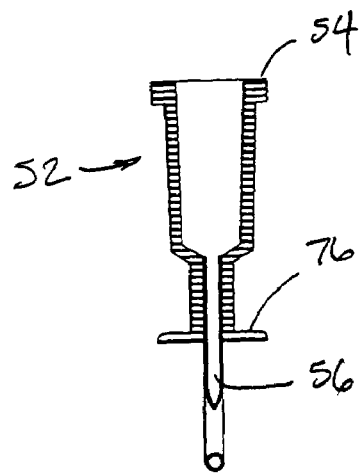
FIG. 6 is a semi-schematic cross-sectional side view of the valve coupler of FIG. 4 taken from a different plane.

FIG. 6 is a cross-sectional side view of the coupler 52 of FIG. 4 taken along a different plane.

Figure 7:
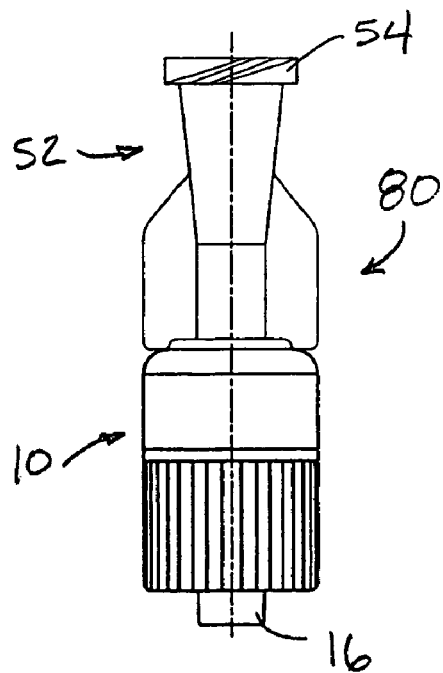
FIG. 7 is a semi-schematic side view of a needleless access port valve assembly provided in accordance with aspects of the present invention; which comprises the coupler in accordance with aspects of the present invention engaged to a valve in accordance with aspects of the present invention.

FIG. 7. is a semi-schematic side view of a needleless access port valve assembly 80 provided in accordance with aspects of the present invention, which comprises the coupler 52 matingly engaged to the valve 10. While not shown, it is understood that the valve assembly 80 is configured to mate with a first medical implement at the inlet 54 of the coupler 52 and with a second medical implement at the outlet 16 of the valve 10 to provide fluid communication between the first medical implement and the second medical implement.

Figure 8:
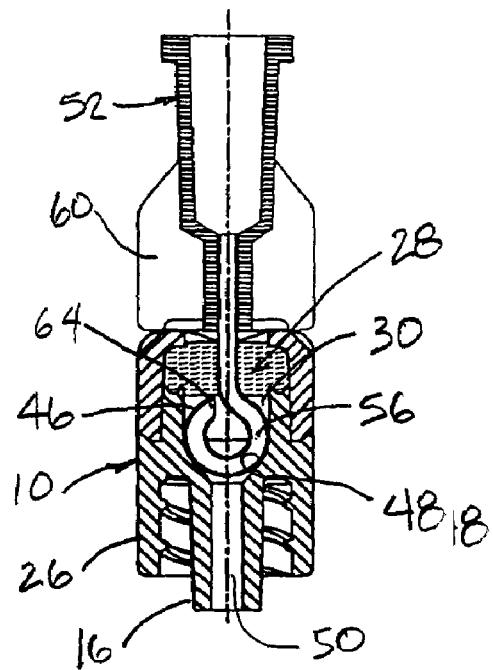
FIG. 8 is a semi-schematic cross-sectional side view of the valve assembly of FIG. 7.

With reference to FIG. 8 in addition to FIG. 2, the coupler 52 is engaged to the valve 10 by inserting the outlet 56 of the coupler, i.e., the tubing 58, through the slit 36 in the septum 28 of the valve and then rotating the coupler plus or minus 5 to 175 degrees; Preferably, the coupler is rotated plus or minus 90 degrees so as to turn the eye-hook shape outlet transversely relative to the length of the slit.

The upper interior cavity section 46 and the taper lower interior cavity section 48 of the interior cavity 30 are sized to accommodate the outlet 56 and preferably contact the outlet when the same is inserted therein. The contact between the taper lower section 48 and the eye-hook shape outlet 56 acts as a depth gauge for gauging the insertion of the outlet 56 before the same is rotated. The contact between the septum 28 and the upper curved section of the outlet serves as a pivoting point. Optionally, one or more tabs or projections may be incorporated in the interior cavity to delimit the rotation of the outlet 56. The one or more tabs may be placed in the interior cavity 30 to control the direction of rotation as well as the degree of rotation of the outlet 56.

Fluid flowing from the coupler 52 will pass through the interior luer taper section 74, then through the tubing 58 and out the outlet opening 64 of the outlet 56. The fluid will then flow through the interior cavity 30 and out the cylindrical section 50 of the outlet 16. The valve 10 is primarily a neutral valve in that no significant positive or negative flush can be detected upon insertion and removal of the outlet 56 from the septum 28.

Figure 9:
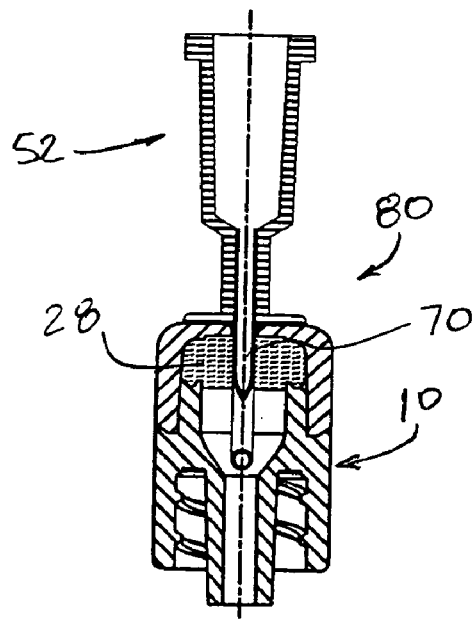
FIG. 9 is a semi-schematic cross-sectional side view of the valve assembly of FIG. 7 taken from a different plane

FIG. 9 is a semi-schematic cross-sectional side view of the valve assembly 80 of FIG. 7 taken from a different plane. The septum 28 compresses around the upper section 70 of the outlet to form a seal around the upper section. When the outlet 56 is rotated in the opposite direction to uncouple the coupler 52 from the valve 10, the slit 36 in the septum 28 is automatically resealed by the compression on the septum from the wall structure of the interior cavity.

Although limited embodiments of the needleless access valve assemblies and their components have been specifically described and illustrated herein, many modifications and variations will be apparent to those skilled in the art. For example, the various valves may incorporate luer-slips rather than luer threads, the tubing may incorporate holes along the length of the eye-hook for increased outlets, and the plastic material may be other than as expressly set forth. Furthermore, it is understood and contemplated that features specifically discussed for one valve embodiment may be adopted for inclusion with another valve embodiment, provided the functions are compatible. Accordingly, it is to be understood that the valve assemblies and their components constructed according to principles of this invention may be embodied other than as specifically described herein. The invention is also defined in the following claims.

What is claimed is:

1. A needleless access port valve assembly comprising a coupler comprising an inlet and an outlet and a valve comprising an inlet, an outlet, and a cavity comprising a tapered base located therebetween; wherein the outlet of the coupler comprises a port comprising a round eye-hook and the inlet of the valve comprises a septum; and wherein the septum is configured to receive the port and the round eye-hook is configured to rotate relative to the septum so that the round eye-hook is wedged between the septum and the tapered base to prevent the round eye-hook from separating from the septum.

2. The needleless access port valve of claim 1, wherein the inlet of the coupler comprises a threaded luer.

3. The needleless access port valve of claim 1, wherein the coupler comprises a pair of fins.

4. The needleless access port valve of claim 1, wherein the valve comprises a two-part housing.

5. The needleless access port valve of claim 4, wherein the two-part housing is welded along a seam.

6. The needleless access port valve of claim 4, wherein the septum is disposed between an upper housing part and a lower housing part of the two-part housing.

7. The needleless access port valve of claim 6, wherein the outlet comprises a male threaded luer.

8. The needleless access port valve of claim 1, wherein the coupler comprises a housing over-molded to the round eye-hook.

9. The needleless access port valve of claim 1, wherein the septum comprises a seam.

10. The needleless access port valve of claim 1, further comprising at least one indentation on a top surface of the valve.

11. A needleless access port valve assembly comprising a coupler matingly engaged to a valve; the coupler comprising an inlet for mating with a first medical implement and the valve comprising an outlet for mating with a second medical implement, wherein the engagement between the coupler and the valve comprises a port comprising a round eye-hook having a fluid opening projecting through a septum and the round eye-hook wedged against the septum to prevent the port from retracting away from the septum.

12. The needleless access port valve of claim 11, wherein the inlet of the coupler comprises a threaded luer.

13. The needleless access port valve of claim 11, wherein the coupler comprises a pair of fins.

14. The needleless access port valve of claim 11, wherein the port is made from a metal material.

15. The needleless access port valve of claim 11, wherein the coupler comprises a housing and the port comprises a linear section extending distally from the housing.

16. The needleless access port valve of claim 11, wherein the valve comprises a two-part housing.

17. The needleless access port valve of claim 16, wherein the septum is disposed in between an upper housing part and a lower housing part of the two-part housing.

18. The needleless access port valve of claim 17, wherein the two-part housing is welded along a seam.

19. The needleless access port valve of claim 11, wherein the outlet comprises a male threaded luer.

20. The needleless access port valve of claim 11, wherein the septum comprises a slit.

21. The needleless access port valve of claim 11, further comprising at least one indentation on a top surface of the valve.

22. A needleless access port valve assembly comprising a coupler matingly engaged to a valve comprising a housing, the coupler comprising a port having a distal section projecting through a slit of a septum in the valve, the distal section comprising a first profile when in a first orientation for projecting through the slit and a second wider profile when in a second orientation for preventing separation of the port from the septum, and wherein the distal section of the port comprises a round eye-hook that touches both the septum and the housing in the second orientation.

23. A needleless access port valve assembly comprising a coupler matingly engaged to a valve, the coupler comprising a port having a distal section projecting through a slit of a septum in the valve, the distal section comprising a first profile when in a first orientation for projecting through the slit and a second wider profile when in a second orientation for preventing separation of the port from the septum, and wherein the distal section of the port comprises a round eye-hook.

24. The needleless access port valve assembly of claim 23, wherein the valve comprises a two-part housing.

25. The needleless access port valve assembly of claim 23, wherein wherein the coupler comprises a threaded inlet luer.

26. The needleless access port valve assembly of claim 23, wherein wherein the valve comprises a threaded outlet luer.

27. The needleless access port valve assembly of claim 22, wherein the valve comprises a two-part housing.

28. The needleless access port valve assembly of claim 22, wherein the coupler comprises a threaded inlet luer.

29. The needleless access port valve assembly of claim 22, wherein the valve comprises a threaded outlet luer.

30. The needleless access port valve assembly of claim 22, wherein the port is made from a metal material.

* * * * *